US008435998B2

(12) United States Patent
Wieser et al.

(10) Patent No.: US 8,435,998 B2
(45) Date of Patent: May 7, 2013

(54) CRYSTALLINE FORM OF POSACONAZOLE (75) Inventors: Josef Wieser, Kundl (AT); Arthur Pichler, Kundl (AT); Andreas Hotter, Kundl (AT); Ulrich Griesser, Innsbruck (AT); Christoph Langes, Innsbruck (AT)

(73) Assignee: Sandoz AG, Basel (CH)

(*) Notice: Subject to any disclaimer, the term of this patent is extended or adjusted under 35 U.S.C. 154(b) by 181 days.

(21) Appl. No.: 12/993,351

(22) PCT Filed: Jun. 25, 2009

(86) PCT No.: PCT/EP2009/057975
§ 371 (c)(1),
(2), (4) Date: Nov. 18, 2010

(87) PCT Pub. No.: WO2010/000668
PCT Pub. Date: Jan. 7, 2010

(65) Prior Publication Data
US 2011/0065722 A1    Mar. 17, 2011

Related U.S. Application Data (60) Provisional application No. 61/133,852, filed on Jul. 3, 2008.

(30) Foreign Application Priority Data
Jul. 3, 2008   (EP) ................... 08159600

(51) Int. Cl.
*A61K 31/496* (2006.01)
*C07D 405/14* (2006.01)

(52) U.S. Cl.
USPC .................... 514/254.07; 544/366

(58) Field of Classification Search .......... None
See application file for complete search history.

(56) References Cited

U.S. PATENT DOCUMENTS

| | | | |
|---|---|---|---|
| 4,533,254 A | 8/1985 | Cook | |
| 4,957,730 A | 9/1990 | Bohn | |
| 5,625,064 A | 4/1997 | Andrews | |
| 5,834,472 A | 11/1998 | Sangekar | |
| 5,972,381 A | 10/1999 | Sangekar | |
| 6,713,481 B1 | 3/2004 | Andrews | |
| 6,958,337 B2 | 10/2005 | Andrews | |
| 2011/0105525 A1* | 5/2011 | Wieser et al. ............ 514/254.07 |

FOREIGN PATENT DOCUMENTS

| | | | |
|---|---|---|---|
| EP | 1021439 B1 | 4/1999 | |
| EP | 2130540 A1 | 12/2009 | |
| EP | 2141159 A1 | 1/2010 | |
| WO | 9517407 A1 | 6/1995 | |
| WO | 9638443 A1 | 12/1996 | |
| WO | 9918097 A | 4/1999 | |
| WO | 02080678 A1 | 10/2002 | |
| WO | 2005117831 A1 | 12/2005 | |
| WO | 2006130177 A | 12/2006 | |
| WO | 2007143390 A | 12/2007 | |
| WO | 2011003992 A1 | 1/2011 | |

OTHER PUBLICATIONS

Saksena, Novel Analogs of Sch 51048; Synthesis and Preliminary Structure Activity Relationships, Abstracts of the 35th Interscience Conference on Antimicrobial Agents and Chemotherapy, Sep. 1995, San Francisco, CA.
Saksena A. K. et al., "Stereoselective Grignard additions to N-formyl hydrazone: a concise synthesis of Noxafil<R> side chain and a synthesis of Noxafil <R>", Tetrahedron Letters, Elsevier, Amsterdam, vol. 45, No. 44, Oct. 25, 2004, p. 8249-8251, figure 4.
Caira M R, "Crystalline Polymorphism of Organic Compounds", Topics in Current Chemistry, Springer, Berlin, DE, vol. 198, Jan. 1, 1998, p. 163-208.
Medema J, Campagne A.: A Simple Method to Determine Cumulative Surface-Area Distributions of Porous Solids; Journal of Catalysis, vol. 8, Issue 2, pp. 120, 1967.
European Pharmacopeia (EP) 6, 2008, method 2.9.31, (No author cited).
International Search Report and Written Opinion (for co-pending WO 2009/147075 under 16508-52680), (2009).
Bennett et al., "Hydroxylated analogues of the orally active broad spectrum antifungal, Sch 51048 (1), and the discovery of posaconazole" Bioorganic & Medicinal Chemistry Letters, Pergamon, Elsevier Science, GB, vol. 16, No. 1, Jan. 1, 2006, p. 186-190.
International Search Report (mailed Sep. 1, 2009) and Written Opinion of International Searching Authority (mailed Sep. 1, 2009), for PCT/EP2009/057975.
Saksena, et. al., "Advances in the Chemistry of Novel Broad-Spectrum Orally Active Azole Antifungals: Recent Studies Leading to the Discovery of SCH 56592," Special Publication-Royal Society of Chemistry, 198(Anti-Infectives pp. 180-199, 1997.
Zhou, Weicheng et al., "Progress in syntheses of azole antifungal agents" Zhongguo Yiyao Gongye Zazhi, 37(2), p. 125-133 Coden: Zygzea; ISSN: 1001:8255, 2006.
US-Pharmacopeia (USP) 32, 2009, method 429, pp. 155-158 (No author cited).
US-Pharmacopeia (USP) 32, 2009, method 711, pp. 263-271 (No author cited).
International Preliminary Report on Patentability and Written Opinion of the International Searching Authority (issued Jan. 5, 2011), for PCT/EP2009/057975.

\* cited by examiner

*Primary Examiner* — Emily Bernhardt
(74) *Attorney, Agent, or Firm* — Jeffrey S. Melcher; Manelli Selter PLLC (57) ABSTRACT

The present invention relates to crystalline form IV of posaconazole and pharmaceutical compositions comprising the same. The pharmaceutical composition can be used to treat or prevent fungal infections.

16 Claims, 6 Drawing Sheets

- x - Crystalline Form IV of posaconazole
- ◆ - Crystalline Form I of posaconazole micronized
- △ - Crystalline Form I of posaconazole non-micronized

CRYSTALLINE FORM OF POSACONAZOLE

CROSS-REFERENCE TO RELATED APPLICATIONS

This application is a national stage entry under 35 U.S.C. 371 of International Application No. PCT/EP2009/057975, filed 25 Jun. 2009, designating the United States. This application claims foreign priority under 35 U.S.C. 119 and 365 to European Patent Application No. 08159600.9, filed 3 Jul. 2008. This application claims domestic priority under 35 U.S.C. 120 and 365 to U.S. Provisional Application No. 61/133,852, filed 3 Jul. 2008. The complete contents of these applications are incorporated herein by reference.

FIELD OF THE INVENTION

The present invention relates to crystalline form IV of posaconazole as well as pharmaceutical compositions comprising the same as an active pharmaceutical ingredient. The pharmaceutical composition can be used to treat or prevent fungal infections. Furthermore, methods of preparing crystalline form IV of posaconazole are disclosed.

BACKGROUND OF THE INVENTION

Posaconazole (CAS Registry Number 171228-49-2; CAS Name: 2,5-anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threo-pentitol) which is represented by the following general formula (I)

(I)

is known as an antifungal agent. It is available as an oral suspension (40 mg/ml) under the trademark NOXAFIL® from Schering Corporation, Kenilworth, N.J.

WO95/17407 and WO 96/38443 disclose the compound having the general formula (I) and its use in treating fungal infections.

A pharmaceutical composition comprising posaconazole, at least one non-ionic surfactant and a diluent is disclosed in WO 02/80678, e.g. in the form of a liquid suspension. WO 02/80678 also describes that for use in its suspension posaconazole is to be micronized, e.g. by microfluidization to obtain a specific particle size in the range of about 1000 nm (nanometers) to about 1800 nm to obtain enhanced bioavailability. The reduction of the particle size is carried out during the preparation of the posaconazole active ingredient and/or during the manufacture of the pharmaceutical composition. A solid solution of posaconazole, which can be provided in the form of a tablet or capsule, is disclosed in U.S. Pat. No. 5,972,381. Other pharmaceutical compositions prepared by mixing or granulating posaconazole with a non-ionic surfactant and a diluent which may be formulated into capsules or tablets are disclosed in U.S. Pat. No. 5,834,472. A topical form of posaconazole, e.g. a lotion, cream, ointment, or "lacquer nail polish" is described in U.S. Pat. No. 4,957,730 (PENLAC® available from Dermik®). An injectable pharmaceutical suspension comprising posaconazole that is stable when subjected to terminal steam sterilization is disclosed in WO 2005/117831.

As was mentioned above, WO 95/17407 and WO 96/38443 disclose the compound having the general formula (I). However, during prosecution of the subsequently filed European patent application no. 98951994.7, now European patent EP 1 021 439 B1, the applicant declared that the methods disclosed in these publications only lead to the compound of formula (I) as an amorphous solid.

Polymorphism is a phenomenon relating to the occurrence of different crystal forms for one molecule. There may be several different crystalline forms for the same molecule with distinct crystal structures and distinct and varying physical properties like melting point, XRPD spectrum, IR-spectrum and solubility profile. These polymorphs are thus distinct solid forms which share the molecular formula of the compound from which the crystals are made up, however, they may have distinct advantageous physical properties which can have a direct effect on the ability to process and/or manufacture the drug product, like flowability, as well as physical properties such as solubility, stability and dissolution properties which can have a direct effect on drug product stability, dissolution, and bioavailability.

Three polymorphic forms of posaconazole designated as forms I, II and III are described and characterized in WO 99/18097 (U.S. Pat. No. 6,713,481, U.S. Pat. No. 6,958,337). Crystalline forms II and III were found to be unstable under the conditions investigated, so that crystalline form I was considered to be useful in the development of a pharmaceutical product.

There remains a need for alternative polymorphic forms of posaconazole which are more stable than form I when used in a pharmaceutical composition and/or which have properties that make them suitable for bulk preparation and handling. Additionally, there is a need for alternative polymorphic forms of posaconazole which allow improved pharmaceutical processing such as the preparation of pharmaceutical compositions on a commercial scale, in particular without the need to apply time-consuming methods to reduce their particle size. Finally, it would be desirable to provide alternative polymorphic forms of posaconazole which show improved dissolution properties and enhanced bioavailability.

SUMMARY OF THE INVENTION

In one embodiment the present invention relates to crystalline form IV of posaconazole.

Crystalline form IV of posaconazole can be described by an X-ray powder diffraction pattern comprising peaks at 2-theta angles of about 3.2°, 6.6°, 10.9°, 16.9°, 18.4° and 25.1°. The typical precision of the 2-theta values is in the range of ±about 0.2°.

Alternatively, crystalline form IV of posaconazole can be characterized by an attenuated total reflectance infrared spectrum comprising absorption bands at wavenumbers of about 3647 $cm^{-1}$, 3472 $cm^{-1}$, 2867 $cm^{-1}$, 1687 $cm^{-1}$, 1512 $cm^{-1}$, 1230 $cm^{-1}$, 1136 $cm^{-1}$, 916 $cm^{-1}$, 853 $cm^{-1}$, 819 $cm^{-1}$ and 681 $cm^{-1}$. The typical precision of the wavenumber values is in the range of ±about 2 $cm^{-1}$.

Figure 3:
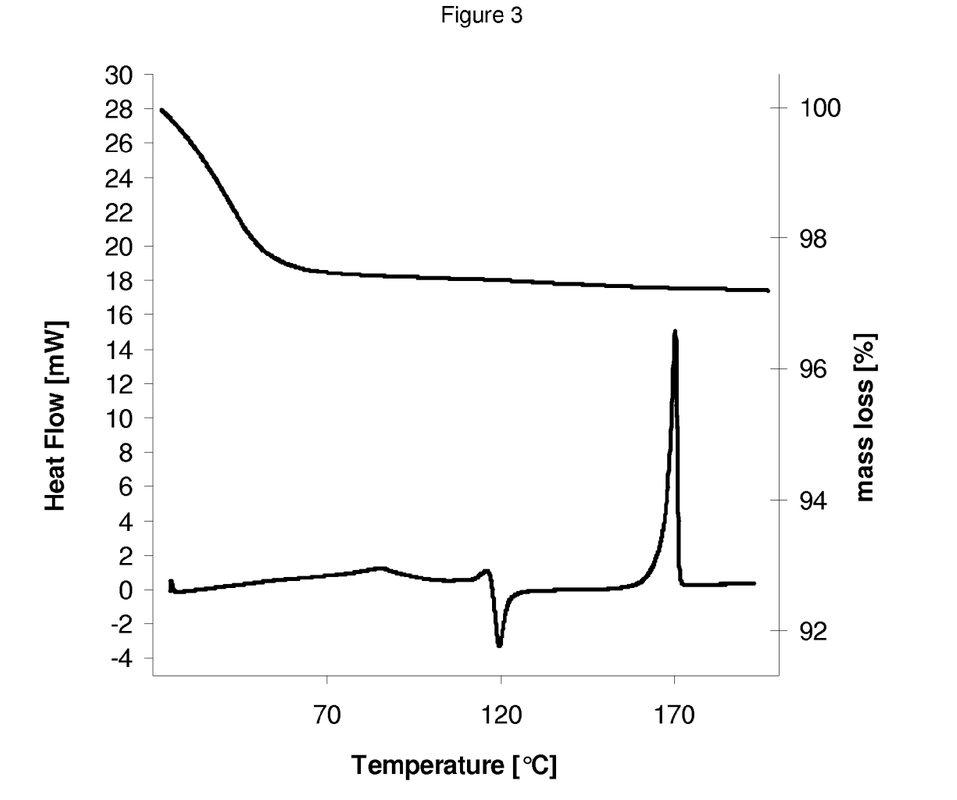
FIG. 3: Thermogravimetric and differential scanning calorimetric curve of form IV of posaconazole. The temperature in ° C. is shown on the x-axis. The heat flow in mW is shown on the left hand ordinate (lower curve), while the mass loss in % is shown on the right hand ordinate (upper curve).

A further method of describing crystalline form IV is by differential scanning calorimetry. A typical differential scanning calorimetry curve of crystalline form IV can be obtained at a heating rate of 10° C./min (10° K/min) and about 2 to 3% mass loss in the TGA analysis (open pan). Typical thermograms of form IV of posaconazole are shown in FIG. 3. It can be seen that the DSC curve of form IV shows a significant dehydration endotherm between about 25° C. and about 105° C. with a subsequent exothermic conversion at about 116° C. ($T_{onset}$ about 113° C.) followed by a peak at about 120° C. ($T_{onset}$ about 117° C.) and melting at about 171° C. with a $T_{onset}$ at about 168° C. (10° C./minute, open pan).

The crystalline form IV of posaconazole typically contains 0 to 1.5 moles water per mole posaconazole.

In one specific embodiment, crystalline form IV of posaconazole has a specific surface area of about 10-25 $m^2$/g±0.5 $m^2$/g.

In another specific embodiment, crystalline form IV of posaconazole has a median particle size of about 0.1-0.2 μm±0.05 μm (micrometers).

Crystalline form IV of posaconazole can be prepared by a process comprising the steps of:
(a) providing a suspension or dispersion of:
  (i) posaconazole, wherein posaconazole is selected from crystalline form III of posaconazole or amorphous posaconazole or a mixture thereof; and
  (ii) water or a mixture of water and methanol; and
(b) allowing the posaconazole to transform to crystalline form IV at a temperature of at most 60° C.

If desired, seed crystals of crystalline form IV of posaconazole can be employed in this process.

Alternatively crystalline form IV of posaconazole can be prepared by a process comprising the steps of:
(a) providing a suspension or dispersion of:
  (i) posaconazole, wherein posaconazole is selected from crystalline form I or II of posaconazole or a mixture thereof;
  (ii) water or a mixture of water and methanol; and
  (iii) seed crystals of crystalline form IV of posaconazole; and
(b) allowing the posaconazole to transform to crystalline form IV at a temperature of at most 60° C.

In the present invention the terms "suspension" and "dispersion" are intended to cover all types of mixtures of solid particles and liquids.

A further embodiment of the present invention relates to a pharmaceutical composition comprising crystalline form IV of posaconazole and optionally a pharmaceutically acceptable carrier.

The crystalline form IV of posaconazole and pharmaceutical compositions comprising it can be used for treating or preventing a fungal infection.

Surprisingly, crystalline form IV of posaconazole shows improved stability when used in a pharmaceutical composition such as an aqueous suspension or dispersion, e.g. for oral administration. Additionally, crystalline form IV of posaconazole as such, i.e. in a non-micronized form, has a smaller median particle size and a larger specific surface area when compared to known non-micronized crystalline form I of posaconazole. This smaller particle size and larger specific surface area advantageously result in an improved dissolution behaviour of crystalline form IV which is expected to provide improved bioavailability. Due to these advantageous properties, crystalline form IV of posaconazole may be directly used as such, i.e. without the need of reducing the particle size of its crystals e.g. by micronization, for the preparation of a medicament such as a liquid suspension or dispersion. Therefore, the use of crystalline form IV of posaconazole for preparing such suspension or dispersion avoids complex, time consuming and costly micronization techniques which are generally applied for treating known crystalline form I of posaconazole to achieve the desired bioavailability.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

DETAILED DESCRIPTION OF THE INVENTION

The present invention relates to crystalline form IV of posaconazole.

Posaconazole is represented by the following general formula (I)

(I)

Crystalline form IV of posaconazole can be prepared by
(a) providing a suspension or dispersion of:
  (i) posaconazole, wherein posaconazole is selected from crystalline form III of posaconazole or amorphous posaconazole or a mixture thereof; and
  (ii) water or a mixture of water and methanol; and
(b) allowing the posaconazole to transform to crystalline form IV at a temperature of at most 60° C.

Alternatively crystalline form IV of posaconazole can be prepared by a process comprising the steps of:
(a) providing a suspension or dispersion of:
  (i) posaconazole, wherein posaconazole is selected from crystalline form I or II of posaconazole or a mixture thereof;
  (ii) water or a mixture of water and methanol; and
  (iii) seed crystals of crystalline form IV of posaconazole; and
(b) allowing the posaconazole to transform to crystalline form IV at a temperature of at most 60° C.

It has been found that if crystalline form I or II or a mixture thereof is employed as a starting material, seed crystals of crystalline form IV must be present during the transformation. As is mentioned in the scientific discussion, which is available from the website of the EMEA, crystalline form I of posaconazole is used in the medicament NOXAFIL®. It is further explained that the crystal form is controlled as part of the drug substance specification and that there has been no evidence of polymorphic transition on storage as micronised powder, during manufacture or as formulated in the finished product. This is in line with the findings of the present inventors.

Amorphous posaconazole can be obtained as described in WO 95/17407 and WO 96/38443. Crystalline forms I, II and III can be prepared as described in WO 99/18097, U.S. Pat. No. 6,713,481 or U.S. Pat. No. 6,958,337.

The amorphous posaconazole or the crystalline form III or the mixture thereof, which is used as a starting material is typically employed in the form of a powder or small crystals. The powder or small crystals may be used as such, e.g. as originating from the synthesis or may be milled or micronized before the transformation step.

The posaconazole starting material is then mixed with water or a mixture of water and methanol. The ratio of water to methanol (v/v) is not particularly restricted as long as the transformation results in crystalline form IV of posaconazole. Typically the ratio of water to methanol will be in the range of 20:80 to 100:0, preferably 50:50 to 100:0, more preferably 60:40 to 90:10.

The posaconazole starting material will be typically provided in a volume of water or a mixture of water and methanol, so that the major part is not dissolved. The mixture is typically a stirrable suspension or dispersion. The exact volume of the water or the mixture of water and methanol will depend on the amount of methanol and the transformation conditions and can therefore vary.

Typically the weight ratio of posaconazole to water or to the mixture of water and methanol will be in the range of about 0.1 g/100 g to about 20 g/100 g, preferably from about 1 g/100 g to about 20 g/100 g, even more preferably about 2 g/100 g to about 10 g/100 g.

If desired, seed crystals of crystalline form IV of posaconazole can also be present in the mixture to aid transformation.

The mixture of posaconazole, water or mixture of water and methanol and optionally seed crystals is then slurried, so that the posaconazole can transform to crystalline form IV.

The temperature at which the transformation can be conducted will depend on the chosen solvent (i.e. water or a mixture of water and methanol), on the form of posaconazole which is used as a starting material, etc. Typical temperatures for conducting the transformation are about 10° C. to about 60° C., preferably about 20° C. to about 55° C., and more preferably ambient temperature (i.e. about 20 to about 30° C.). The temperature can also vary during the transformation step. However, the suspension or dispersion is not subjected to a refluxing step during the presently claimed processes.

In a preferred embodiment a mixture of water and methanol in the ratio of 4:1 (v/v) is used in steps (a) and (b) of the above described processes and the preferred temperature range is about 15° C. to about 50° C.

The duration of the transformation step is not particularly limited. Generally, the transformation will be conducted until substantially all (e.g., preferably at least 90 wt.-%, more preferably at least 95 wt.-%) of the posaconazole starting material has been transformed into crystalline form IV. Typically for 1 g starting material the transformation step will take from about 1 day to about 20 days, preferably from about 2 days to about 15 days at ambient temperature, if seed crystals are not employed. The transformation will be quicker, e.g. from about 1 hour to about 5 days, preferably about 2 hours to about 4 days at ambient temperature, if seed crystals are employed. If the mixture is kept at a higher temperature the speed of transformation will also be increased. In case water is used to provide the suspension or dispersion mentioned in step (a) of the herein described processes and no seed crystals are employed, the transformation step will take at least about 4 to 7 days at ambient temperature. A skilled person can easily determine appropriate transformation durations according to the batch size, temperature of the suspension/dispersion, presence or absence of seed crystals, etc.

After the transformation step, the product is isolated. Transformation to crystalline form IV can be confirmed by IR or XRPD analysis as described herein.

The resultant crystalline form IV is a polymorphic form of posaconazole. Unlike form II which is a monohydrate and form I which is anhydrous, form IV is a nonstoichiometric hydrate. It typically has a stoichiometry of from 1:0 to 1:1.5 (mole:mole) of posaconazole:water.

Figure 1:
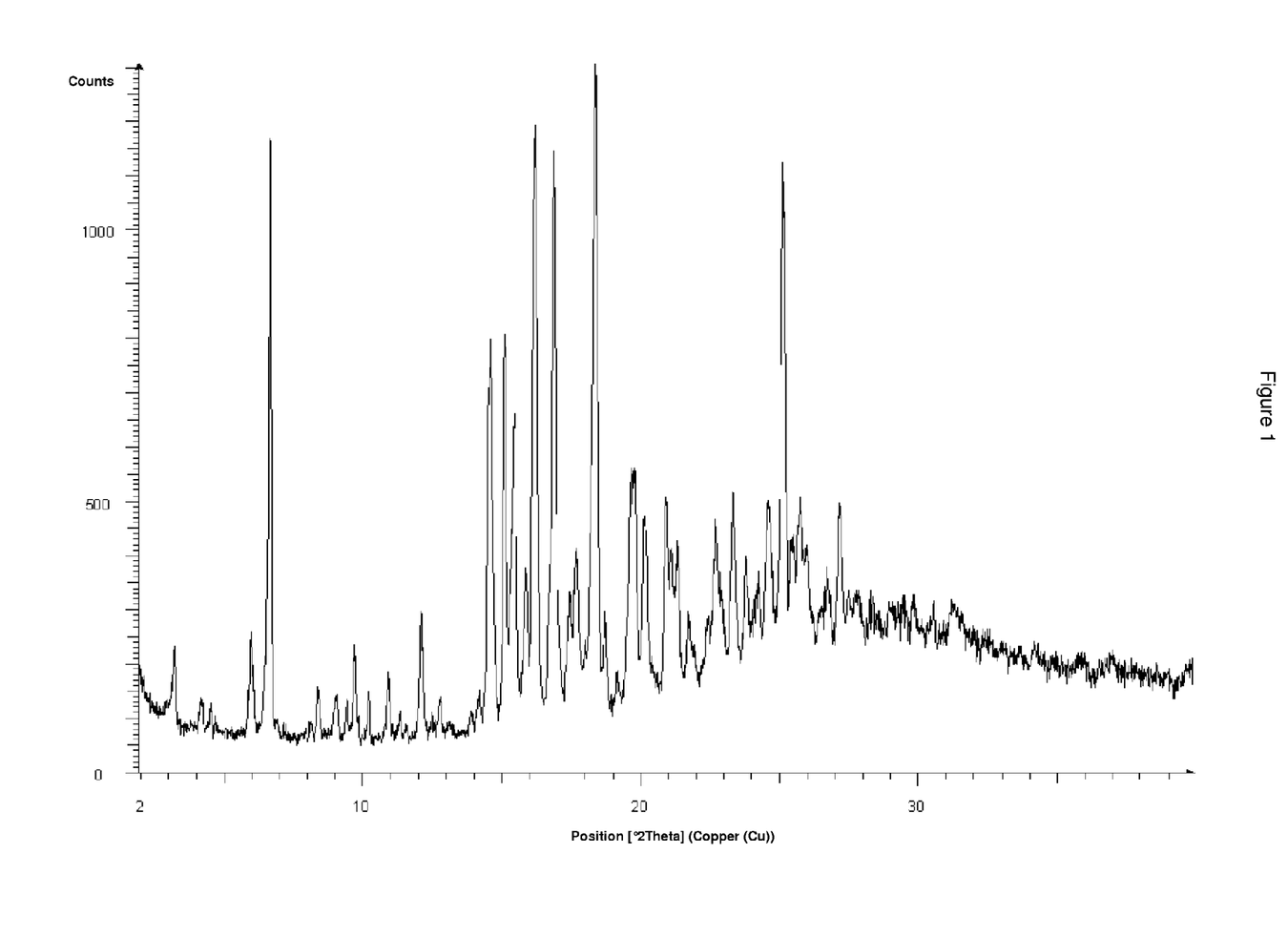
FIG. 1: X-ray powder diffraction pattern of form IV of posaconazole. In this figure the counts per 80 seconds are presented on the y-axis, while the 2 theta values in degrees are presented on the x-axis.

Crystalline form IV can be characterized by an X-ray powder diffraction pattern comprising peaks at 2-theta angles of about 3.2°, 6.6°, 10.9°, 16.9°, 18.4° and 25.1° (± about 0.2°). A characteristic X-ray powder diffraction pattern is shown in FIG. 1.

Figure 2:
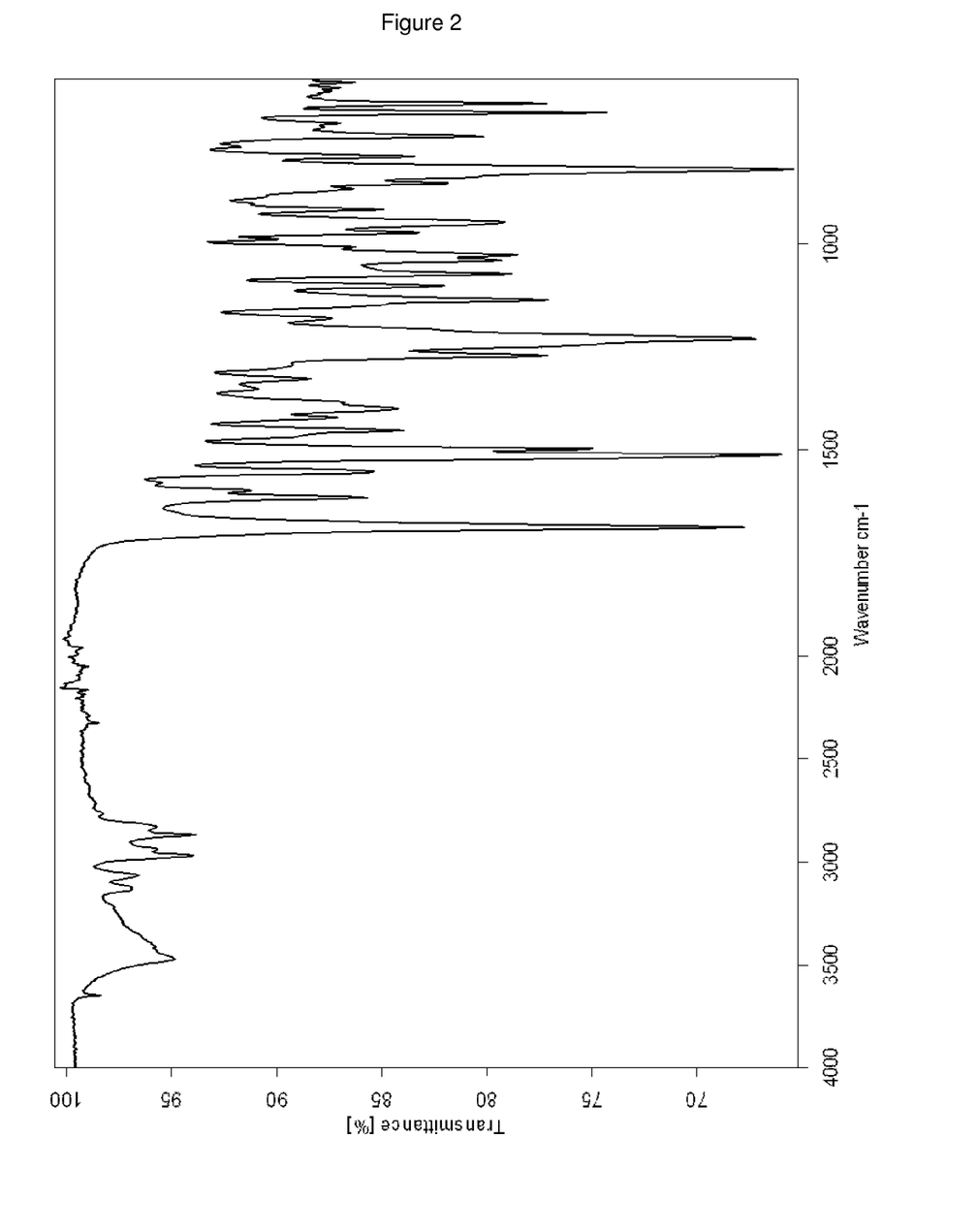
FIG. 2: Infrared spectrum of form IV of posaconazole. The transmittance in % is plotted versus the wavenumber in $cm^{-1}$.

Alternatively, crystalline form IV can be characterized by an attenuated total reflectance infrared spectrum comprising absorption bands at wavenumbers of about 3647 $cm^{-1}$, 3472 $cm^{-1}$, 2867 $cm^{-1}$, 1687 $cm^{-1}$, 1512 $cm^{-1}$, 1230 $cm^{-1}$, 1136 $cm^{-1}$, 916 $cm^{-1}$, 853 $cm^{-1}$, 819 $cm^{-1}$ and 681 $cm^{-1}$ (± about 2 $cm^{-1}$). A typical attenuated total reflectance infrared spectrum is shown in FIG. 2.

A further method for identifying crystalline form IV is differential scanning calorimetry. A typical differential scanning calorimetry curve of crystalline form IV can be obtained at a heating rate of 10° C./min (10° K/min) and about 2 to 3% mass loss in the TGA analysis (open pan). The DSC curve of form IV shows a significant dehydration endotherm between about 25° C. and about 105° C. with a subsequent exothermic conversion at about 116° C. ($T_{onset}$ about 113° C.) followed by a peak at about 120° C. ($T_{onset}$ about 117° C.) and melting at about 171° C. with a $T_{onset}$ at about 168° C. (10° C./minute; open pan). A characteristic curve is shown in FIG. 3.

Crystalline form IV of posaconazole is preferably substantially pure and substantially free of other polymorphic forms or of amorphous posaconazole. Thus, crystalline form IV of posaconazole preferably shows a polymorphic purity of at least about 90 wt.-%, more preferably of at least about 95 wt.-% and most preferably of at least about 98 wt.-% as measured by XRPD analysis as herein described.

The present inventors have surprisingly found that the new polymorph, crystalline form IV, has improved stability when used in a pharmaceutical composition such as in an aqueous suspension or dispersion, e.g. for oral administration, as herein described. Furthermore, crystalline form IV is suitable for bulk preparation and handling. In addition it has the water solubility required for the preparation of the above mentioned pharmaceutical composition.

Advantageously, crystalline form IV is expected to have an improved rate and possibly also extent of absorption due to its water solubility which is one important factor positively influencing bioavailability—in particular when combined with its small particle size and large specific surface area as described in detail below. This is especially important with posaconazole, because it is a highly lipophilic base (log P>3, pKa 3.6 and 4.6).

Crystalline form IV is stable under storage conditions which are typical for pharmaceutical compositions and is thus suitable for the preparation of medicaments. Typical storage conditions are, for example, storage at ambient temperature, such as about 20° C. to about 30° C., for several months (e.g., for at least 5 months, preferably at least 12 months, more preferably at least 24 months) in a closed vial.

In experiments crystalline form IV was stable during storage for 63 days at ambient temperature. Even when stored for 4 weeks at 40° C., crystalline form IV was stable.

In this context, "stable" means that neither degradation nor polymorphic conversion to another polymorphic form of crystalline form IV can be detected, for example by HPLC, IR or XRPD analysis as defined herein.

Even if suspended in water and stirred for 1 week at ambient temperature, crystalline form IV of posaconazole is not susceptible to transformation into another form.

Moreover, if suspended in a pharmaceutical composition such as an aqueous suspension as herein described, and stirred for 1 week at ambient temperature, crystalline form IV of posaconazole shows polymorphic stability in the sense that no conversion to another polymorphic form is observed by measuring the X-ray Powder Diffraction Pattern as herein described (see also Example 6).

Figure 5:
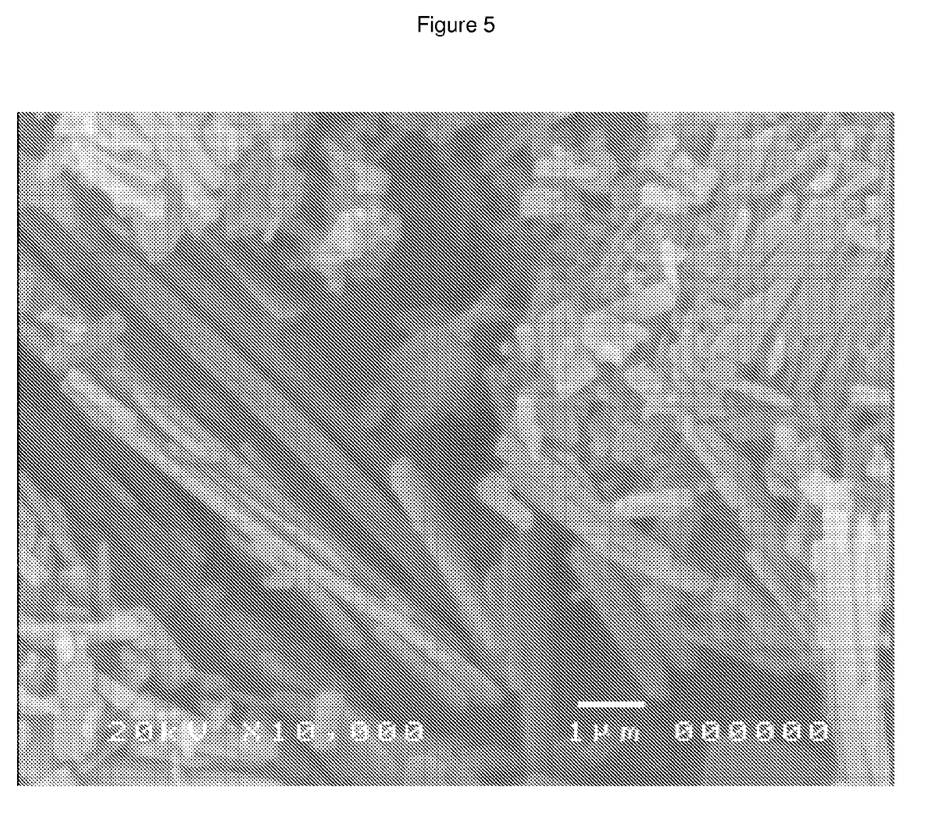
FIG. 5: Morphology and shape of crystals of Form IV of posaconazole as measured by scanning electron microscopy (SEM)

Crystalline form IV of posaconazole consists of a large amount of a very fine fraction of rod-shaped particles with typical dimensions of 0.1-0.2 μm and a fraction of bigger and also rod-shaped crystals with about 0.3 μm thickness and a length of about 2-6 μm. A typical picture of crystals of form IV of posaconazole is seen in FIG. 5 showing a scanning electron microscopy (SEM) picture as obtained by low vacuum scanning electron microscopy, (pressure: about 8 Pa, backscattered electron detector, 20 kV electron acceleration voltage) from crystalline form IV of posaconazole as prepared according to the method of Example 4.

Figure 6:
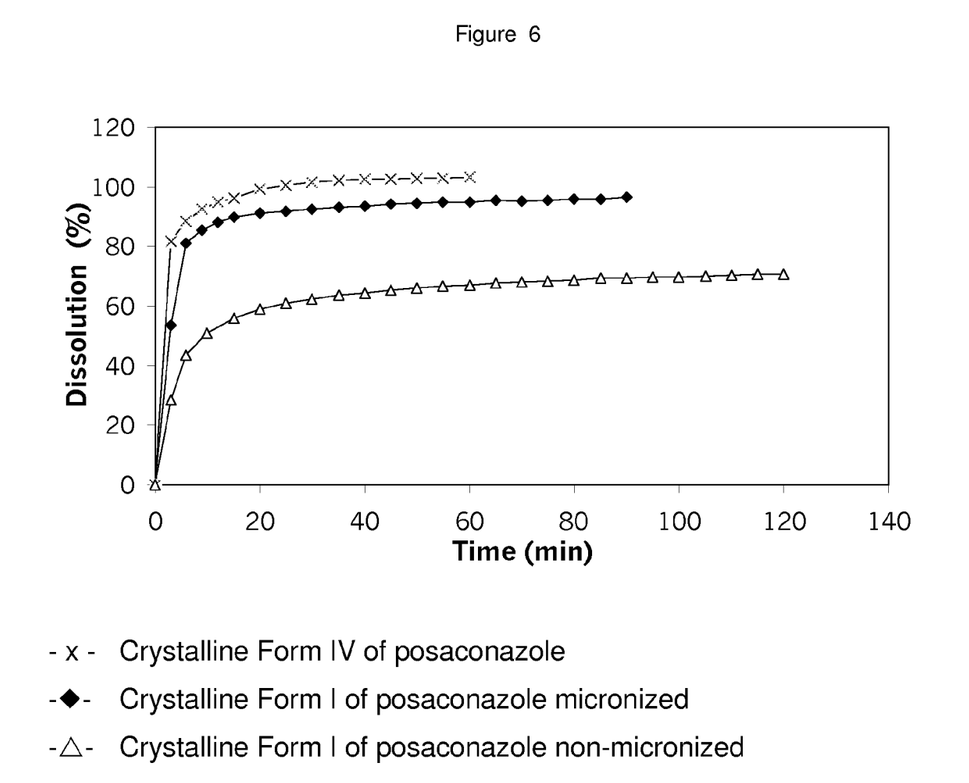
FIG. 6: Dissolution of crystalline form IV of posaconazole as compared to that of crystalline form I of posaconazole. The amount of posaconazole dissolved in % is plotted versus time in minutes.

The specific surface area of crystalline form IV of posaconazole as such, i.e. as obtained according to the herein described methods, is typically about 10-25 $m^2/g$±0.5 $m^2/g$, e.g. about 13-20 $m^2/g$±0.5 $m^2/g$, such as about 15-17 $m^2/g$±0.5 $m^2/g$, as measured according to the known Multi-Point-BET-method as herein described and as shown in Example 7. This specific surface area of crystalline form IV of posaconazole is about 10-fold larger when compared to that of known crystalline form I. It is known that the specific surface area between a solid and a liquid phase has a direct impact on the dissolution rate and thus on the bioavailability of the pharmaceutical ingredient as described e.g. by the equation by Nernst and Brunner as found in W. Nernst, Z. Phys. Chem. 47 (1904), pp. 52-55. Therefore, as a higher specific surface area value results in a higher dissolution rate, crystalline form IV of posaconazole is expected to exhibit a better dissolution behaviour and consequently a better bioavailability when compared to crystalline form I. Indeed, Example 9 and FIG. 6 show that crystalline form IV of posaconazole as such, i.e. in its non-micronized form—when contained in a suspension—shows a faster dissolution when compared to non-micronized form I. Moreover, non-micronized crystalline form IV of posaconazole shows even a slightly faster dissolution when compared to micronized form I. This improved dissolution behaviour is also shown in FIG. 6. Thus, crystalline form IV of posaconazole may advantageously be used as such, i.e. without being micronized, for preparing a pharmaceutical composition, e.g. a liquid suspension or dispersion as herein described—in contrast to known posaconazole forms which are micronized for use in such suspensions as e.g. described in WO 02/80678.

Crystalline form IV of posaconazole can be used as a medicament to treat or prevent any of the disorders which can be treated or prevented by posaconazole. In particular, crystalline form IV can be used for treating or preventing fungal infections, especially in mammals, such as humans. Thus, a method of treating or preventing a fungal infection by administering a therapeutically effective amount of crystalline form IV of posaconazole to a patient in need thereof is also contemplated. Crystalline form IV is suitable for treating or preventing a wide range of infections caused by fungal pathogens, including yeasts, dermatophytes and molds. Typical fungal infections which can be treated or prevented are those caused by *Aspergillus, Blastomyces, Candida, Cryptococcus, Coccidioides, Epidermophyton, Fonsecaea, Fusarium, Mucor, Saccharomyces, Torulopsis, Trichophyton, Trichosporon, Sporothrix* and *Pneumocysitis*, particularly *Candida* and *Aspergillus*.

Typical fungal infections which can be treated or prevented are invasive infections, which most often occur in immunocompromised patients, such as organ transplant patients, cancer patients undergoing chemotherapy, hematopoietic stem cell transplant (HSCT) recipients with graft-versus-host disease (GVHD), and patients with hematologic malignancies with prolonged neutropenia from chemotherapy. Examples of fungal infections which can be treated or prevented are oropharyngeal candidiasis, including oropharyngeal candidiasis refractory to itraconazole and/or fluconazole, fusariosis, chromoblastomycosis, mycetoma, and coccidioidomycosis and invasive aspergillosis refractory to amphotericin B or itraconazole.

The crystalline form IV of posaconazole may thus be used for the preparation of a medicament for treating or preventing a fungal infection.

Usually most of the posaconazole present in the pharmaceutical composition will be crystalline form IV although certain amounts of other crystalline forms or of amorphous posaconazole can also be present. Preferably at least about 90 wt.-%, more preferably at least about 95 wt.-%, and most preferably at least about 98 wt.-% of the posaconazole present in the pharmaceutical composition is crystalline form IV.

Crystalline form IV of posaconazole can be administered alone or in combination with other pharmaceutically active compounds such as a further antifungal agent. In this case, the crystalline form IV of posaconazole and the other pharmaceutically active compound can be administered either simultaneously or sequentially.

The pharmaceutical composition comprising the crystalline form IV is not particularly limited and it can be formulated according to known principles, e.g. either alone or together with at least one pharmaceutically acceptable additive.

Crystalline form IV of posaconazole can be administered according to any appropriate route. Typically, the pharmaceutical composition will be adapted for oral, parenteral (SC, IM, IV and IP), topical or vaginal administration or administration by inhalation (orally or intranasally), preferably for oral, parenteral or topical administration.

Dosage forms for oral administration include tablets, capsules, lozenges, pills, wafers, granules, oral liquids such as syrups, suspensions, dispersions, solutions, emulsions, cachets, powders and powders for reconstitution.

Dosage forms for parenteral administration include solutions or emulsions for infusion, solutions, suspensions, dispersions or emulsions for injection, pre-filled syringes, and/or powders for reconstitution.

Dosage forms for local/topical administration comprise insufflations, aerosols, metered aerosols, transdermal therapeutic systems, medicated patches, solutions, suspensions, emulsions, lotions, creams or ointments suitable for application to the skin, rectal suppositories, and/or ovula.

The pharmaceutical compositions of the invention can be produced in a manner known per se to the skilled person as described, for example, in Remington's Pharmaceutical Sciences, 15th Ed., Mack Publishing Co., New Jersey (1991).

Pharmaceutical compositions according to the invention contain crystalline form IV as the active ingredient and optionally at least one pharmaceutically acceptable additive. Any pharmaceutically acceptable additive can be employed as long as it does not detrimentally affect the properties of the pharmaceutical composition. Examples of typical pharmaceutically acceptable additives comprise carriers (e.g., solid carriers such as magnesium carbonate, magnesium stearate, talc, sugar, lactose, pectin, dextrin, starch, gelatin, tragacanth, methylcellulose, sodium carboxymethyl-cellulose and wax; or liquid carriers such as water, aqueous or less preferably non-aqueous liquids), vehicles, diluents, solvents, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers, additives to make solutions isotonic, antifoaming agents, encapsulating material, surfactants (particularly non-ionic surfactants), opacifying agents, enhancers, waxes, cap anti-locking agents (e.g. glycerol) and ion exchange resins.

Other suitable pharmaceutically acceptable additives are described e.g. in Remington's Pharmaceutical Sciences, 15th Ed., Mack Publishing Co., New Jersey (1991).

The pharmaceutical composition may be a solid or liquid. Solid compositions include powders, tablets, dispersible granules, capsules, cachets, and suppositories. In this embodiment, the pharmaceutically acceptable additive can be one or more substances mentioned above and particularly be selected from carriers, diluents, flavoring agents, solubilizers, lubricants, suspending agents, binders or disintegrants. In powders, the additive can be a finely divided solid which is in admixture with the finely divided active compound. Suitable solid carriers are well-known in the art and include magnesium carbonate, magnesium stearate, talc, sugar, lactose, pectin, dextrin, starch, gelatin, tragacanth, methylcellulose, sodium carboxymethyl-cellulose and wax.

The pharmaceutically acceptable additive can also be an encapsulating material. The term "composition" is intended to include the formulation of the active ingredient with encapsulating material providing a capsule in which the active ingredient (with or without other additives) is surrounded by an encapsulating material, which is thus in association with it. Similarly, cachets are included. Tablets, powders, cachets and capsules can be used as solid dosage forms suitable for oral administration.

Topical formulations containing crystalline form IV normally contain one or more non-toxic, pharmaceutically acceptable topical carriers and may be in the form of, e.g., a solution, suspension, emulsion, lotion, cream or ointment which is suitable for application to the skin of a mammal, in particular of a human patient. Topical formulations containing crystalline form IV which can be useful for nasal or ophthalmic administration are also contemplated. Ophthalmic formulations may also be ointments.

Typical formulations and indications for posaconazole are described, for example, in WO95/17407, WO96/38443, WO02/80678, WO2005/117831, WO99/18097, U.S. Pat. No. 5,972,381, U.S. Pat. No. 5,834,472, and U.S. Pat. No. 4,957,730. It is to be noted that these patents and patent applications are given as an example only and that this list is not exhaustive.

Due to its water solubility, in particular in combination with its large specific surface area and its small particle size as herein described, crystalline form IV is especially suitable for liquid pharmaceutical formulations, in particular for oral administration such as suspensions or dispersions, e.g. aqueous suspensions or dispersions.

Aqueous suspensions or dispersions of crystalline form IV of posaconazole are particularly stable and thus crystalline form IV is especially useful in the preparation of oral suspensions or dispersions.

In one preferred embodiment, the pharmaceutical composition is in the form of an aqueous suspension or dispersion comprising crystalline form IV of posaconazole and a non-ionic surfactant and optionally at least one thickening agent. Examples of non-ionic surfactants and thickening agents are disclosed in WO 02/80678. As these thickening agents facilitate suspension of the pharmaceutical composition, they may also be considered as suspending agents. The pharmaceutical composition may also optionally contain further additives as mentioned herein and/or known for formulating liquid forms such as antifoaming agents, preservatives, opacifying agents, flavors, sweeteners, diluents, cap anti-locking agents and buffering agents. This pharmaceutical composition is preferably suitable for oral administration. Thus, in one specific embodiment, the pharmaceutical composition is an aqueous suspension or dispersion suitable for oral use which can be made by suspending or dispersing crystalline form IV of posaconazole (preferably having a particle size of less than about 100 μm, more preferably less than about 10 μm, even more preferably less than about 5 μm, most preferably having a size of about 1.5±about 0.5 μm or less than about 1.5± about 0.5 μm), a non-ionic surfactant (such as a sorbitan ester), and optionally at least one thickening agent (e.g. a combination of xanthan gum and a liquid sugar) in a pharmaceutically acceptable liquid carrier (such as purified water).

The median particle size of crystalline form IV of posaconazole when used as such, i.e. in a non-micronized form for preparing a pharmaceutical composition in the form of a liquid suspension or dispersion as herein described, has been determined in samples taken from such suspension. Said median particle size is typically about 0.1-0.2 μm±0.05 μm, e.g. 0.14-0.17 μm, such as 0.15 μm, when measured with known laser diffraction methods, e.g. determination of the particle size distribution (Malvern) according to the US-Pharmacopeia (USP) 32 (2009) method <429> and to the European Pharmacopeia (EP) 6 (2008) method 2.9.31. based on the diffraction of laser by particles within the measurement volume (for details see Example 8). In the present invention, the term median particle size is understood to mean the d(0.5) value as determined according to the herein described laser diffraction methods.

Therefore and surprisingly, crystalline form IV of posaconazole as such—i.e. in its non-micronized form—shows a considerably smaller median particle size when compared to non-micronized known posaconazole polymorphic forms such as form I. Moreover, non-micronized crystalline form IV of posaconazole shows even a smaller median particle size than micronized form I, e.g. as contained in NOXAFIL® (US product, as available from Medizone Germany GMBH) as is demonstrated in Example 8.

This smaller particle size of crystalline form IV of posaconazole—in particular in combination with its higher specific surface area value—advantageously leads to an improved dissolution behaviour of crystalline form IV of posaconazole, e.g. when contained in a pharmaceutical composition such as a liquid suspension or dispersion. FIG. 6 and Example 9 demonstrate that said smaller particle size of crystalline form IV of posaconazole when contained in an aqueous suspension—in particular in combination with said higher specific surface area value—indeed leads to a distinctly faster dissolution when compared to non-micronized crystalline form I, and to a similar or even slightly faster dissolution when compared to micronized form I. As an improved dissolution behaviour is considered to enhance bioavailability, non-micronized crystalline form IV is expected to have an improved bioavailability as compared to that of non-micronized form I—and a similar and probably slightly better bioavailability as compared to that of micronized form I as contained in known posaconazole suspensions.

Indeed, it is known that for enhancing bioavailability, the particle size of known posaconazole forms—when used for the preparation of a pharmaceutical composition, e.g. for preparation of a suspension—is generally reduced e.g. by micronization in order to obtain a mean particle size range of about 1000 nm to about 1800 nm, e.g. about 1200 nm to about 1600 nm, preferably of 1400 nm, or a median particle size of about 1.4±0.2 μm as described in WO 02/80678. According to WO 02/80678, the preferred method for micronizing posaconazole is microfluidization, e.g. as described in U.S. Pat. No. 4,533,254 which is a complex, time consuming and costly technique.

In contrast to known posaconazole forms such as crystalline form I as contained in known suspensions, e.g. NOXAFIL®, crystalline form IV of posaconazole may advantageously be used for the preparation of the herein described pharmaceutical compositions, e.g. suspensions or dispersions, without the need to be micronized. Thus, the use of crystalline form IV of posaconazole for preparing the above mentioned pharmaceutical compositions avoids any such costly and time consuming micronization techniques as herein mentioned. In other words, when using crystalline form IV of posaconazole as starting material for preparing pharmaceutical compositions, e.g. a liquid suspension or dispersion, advantageously there is no need to reduce its particle size, i.e. the particle size of its crystals, e.g. by conventional micronization techniques such as microfluidization or milling, before or during the manufacture of said composition. As a consequence, complex particle size monitoring procedures required during such laborious micronization steps are avoided. Additionally, the use of crystalline form IV of posaconazole for preparing these compositions reduces the number of steps of particle size control required throughout the manufacturing process, firstly because no such control is necessary for crystalline form IV as such, i.e. as used before starting the first step of said manufacturing process, and secondly because the above mentioned particle size monitoring steps necessitated during micronization are not required.

Therefore, crystalline form IV of posaconazole may be used in a non-micronized form, e.g. having a median particle size of about 0.1-0.2 μm±0.05 μm for the preparation of a medicament, e.g. a pharmaceutical composition, e.g. a suspension or dispersion, such as an aqueous suspension or dispersion, for treating or preventing a fungal infection.

Optionally, and if ever potentially desired, crystalline form IV of posaconazole is advantageously also suitable for particle size reduction by conventional techniques such as micronization or milling techniques.

One specific example of a pharmaceutical composition in the form of a liquid suspension within the scope of the invention is described below:

Example A

| Ingredient | Concentration in mg/ml |
|---|---|
| Posaconazole Form IV | 40 |
| Polysorbate 80 | 10 |
| Sodium Citrate Dihydrate | 0.6 |
| Citric Acid Monohydrate | 1.5 |
| Simethicone | 3 |
| Xanthan Gum | 3 |
| Sodium Benzoate | 2 |
| Liquid Glucose | 350 |
| Glycerol | 100 |
| Artificial Cherry Flavour | 5 |
| Titanium Dioxide | 4 |
| Purified Water, q.s. | Ad 1 ml |

A suspension such as that of Example A may be prepared as follows:

about 40% of the final amount of Polysorbat 80 and about 40% of the final amount of Simethicone are mixed and dissolved and/or dispersed in about 12% of the final amount of purified water and homogenized with Ultra Turrax (as commercially available from IKA Werke GmbH, Germany). Subsequently, crystalline form IV of posaconazole is suspended or dispersed in this mixture under homogenization by Ultra Turrax. The remaining about 60% of Polysorbat 80 and of simethicone and about 32% of the final amount of the purified water are added and mixed and optionally homogenized using Ultra Turrax, followed by the addition of sodium benzoate, sodium citrate dihydrate and citric acid monohydrate. After further mixing, xanthan gum is added followed by mixing, e.g. by magnetic stirring, and a hydratization phase without any mixing. Subsequently, glycerol, liquid glucose and titanium dioxide are added under continuous mixing optionally using additionally a suitable homogenizer. Finally, cherry flavour and the remaining portion of about 56% of the final amount of purified water are added and mixed until a uniform suspension is obtained.

In one preferred embodiment, crystalline form IV of posaconazole is non-micronized, i.e. it has a median particle size of about 0.1-0.2 μm±0.05 μm when used in the above described composition.

In another embodiment, the pharmaceutical composition is in a solid form, e.g., in the form of a powder or of granules, which might be used to prepare a liquid form, such as a suspension or dispersion as described herein.

Parenteral forms to be injected intravenously, intramuscularly, or subcutaneously may generally be in the form of a sterile solution, and may contain additives such as salts or glucose to make the solution isotonic.

The dosage of crystalline form IV of posaconazole can be determined by a skilled physician and will depend on various factors such as the disorder to be treated, its severity, the mode of administration, the sex, age and weight of the patient, etc. Typically about 1 to about 30 mg/kg body weight per day, more typically about 1 to about 20 mg/kg body weight per day, even more typically about 1 to about 10 mg/kg body weight per day will be given for oral administration, while from about 0.25 mg/kg body weight per day to about 20 mg/kg body weight per day, preferably from about 0.5 mg/kg body weight per day to about 10 mg/kg body weight per day, will be applied via parenteral administration.

The amount of crystalline form IV within topical formulations can vary. It will typically be from about 0.1% to about 20%, preferably about 0.5% to about 10%, by weight of the total pharmaceutical composition.

The amount of crystalline form IV of posaconazole within the liquid pharmaceutical compositions for oral administration described above can also vary. It may be from about 10 mg/ml to about 100 mg/ml, preferably from about 20 mg/ml to about 60 mg/ml, and e.g. be about 40 mg/ml.

Antifungally effective amounts of the liquid pharmaceutical compositions for oral administration described above and containing e.g. 40 mg/ml of crystalline form IV of posaconazole may be administered orally in doses of 5 ml containing 200 mg of crystalline form IV of posaconazole—three times a day or four times a day—, or in doses of 10 ml containing 400 mg of crystalline form IV of posaconazole—twice a day. The attending physician may change the doses and dosing regimen in view of the age, health and sex of the patient as well as the severity of the disease.

The pharmaceutical compositions will be typically administered daily.

The present invention is illustrated by the following examples, which should not be construed as limiting.

EXAMPLES

The X-ray powder diffraction pattern (XRPD) was obtained with a PANalytical X'Pert PRO diffractometer equipped with a theta/theta coupled goniometer in transmission geometry, Cu—K$\alpha_{1,2}$ radiation (wavelength 0.15419 nm) with a focusing mirror and a solid state PIXcel detector. The patterns were recorded at a tube voltage of 40 kV, tube current of 40 mA, applying a stepsize of 0.007° 2θ with 80 s per step (255 channels) in the angular range of 2° to 40° 2θ at ambient conditions. A typical precision of the 2-theta values is in the range of about ±0.2° 2-theta. Thus a diffraction peak that appears at 5.0° 2-theta can appear between 4.8 and 5.2° 2-theta on most X-ray diffractometers under standard conditions.

Infrared spectra (IR) were collected on a MKII Golden Gate™ Single Reflection Diamond ATR (attenuated total reflection) cell with a Bruker Tensor 27 FTIR spectrometer with 4 cm$^{-1}$ resolution. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, an infrared peak that appears at 1716 cm$^{-1}$ can appear between 1714 and 1718 cm$^{-1}$ on most infrared spectrometers under standard conditions.

Differential scanning calorimetry (DSC) was performed with a DSC 7 (Perkin-Elmer, Norwalk, Conn., USA) using the Pyris software. A sample of about 4 mg was weighed into a 25 μl Al-pan.

Dry nitrogen was used as the purge gas (purge: 20 ml min$^{-1}$). When used herein, the term "$T_{onset}$" determined by Differential Scanning calorimetry means the temperature corresponding to the intersection of the pretransition baseline with the extrapolated leading edge of the transition.

Thermogravimetric analysis was performed with the thermogravimetric system TGA-7 using the Pyris Software for Windows NT (Perkin-Elmer, Norwalk, Conn., USA), 50 μl platinum pans, nitrogen purge gas (sample purge: 20 ml min$^{-1}$, balance purge: 40 ml min$^{-1}$).

Melting points were determined with a Büchi B-545 instrument in automatic mode with a threshold of 40% transmission. Measurements were conducted in pharmacopeia mode at 1.0° C./min heating rate.

The moisture sorption isotherm was recorded with a SPS-11 moisture sorption analyzer (MD Mess-technik, Ulm, D). The measurement cycle was started at 0% relative humidity (RH), increased in 10% steps up to 90% RH and in a 5% step up to 95% RH. The equilibrium condition for each step was set to a constant mass±0.003% over 49 min. The temperature was 25±0.1° C.

HPLC assay was performed using the following conditions:

Column: ZORBAX XDB-C18 Rapid Resolution HT, 1.8 μm, 50×4.6 mm (Agilent Technologies)
Eluent A: Dilute 2 ml of acetic acid (99-100%) with water and fill up to 1000 ml with water. Adjust pH to 6.5 with 2.5% ammonia.
Eluent B: water/acetonitrile=50/50 (v/v)
Flow rate: 0.8 ml/min
Temperature: 40° C.
Detection: UV at 260 nm
Gradient:

| t [min] | 0 | 7.5 | 20 |
|---|---|---|---|
| % B | 35 | 85 | 95 |

Stop time: 20 min
Post time: 5 min
Sample concentration: about 0.5 mg/ml
Solvent: water/acetonitrile=50/50 (v/v)

Example 1

250 mg of posaconazole in amorphous form were suspended in a solution consisting of 5 ml of water and 1.25 ml of methanol. The mixture was stirred at ambient temperature for 6 days. The white suspension was filtered and the product was dried in vacuum overnight to yield 240 mg of a white crystalline solid. The product was analyzed by DSC, FT-IR using an attenuated total reflectance cell as herein described and XRPD and found to be a novel form of posaconazole denominated as form IV.

The melting point of the product of Example 1 was 170.1±0.5° C.

Crystalline form IV obtained according to example 1 has an X-ray powder diffraction spectrum as shown in FIG. 1. Characteristic XRPD angles, d-spacings and relative intensities are shown in Table 1.

TABLE 1

Angles 2 theta, d-values and relative intensities of form IV

| Angle [2-Theta °] | d value [Angstrom] | rel. intensity [%] |
|---|---|---|
| 3.18 | 27.783 | 18 |
| 4.15 | 21.267 | 11 |
| 5.95 | 14.842 | 20 |
| 6.61 | 13.355 | 90 |
| 8.38 | 10.540 | 12 |
| 9.01 | 9.805 | 11 |
| 9.40 | 9.401 | 10 |
| 9.67 | 9.143 | 18 |
| 10.89 | 8.117 | 15 |

TABLE 1-continued

Angles 2 theta, d-values and relative intensities of form IV

| Angle [2-Theta °] | d value [Angstrom] | rel. intensity [%] |
|---|---|---|
| 12.09 | 7.314 | 23 |
| 12.75 | 6.938 | 10 |
| 14.60 | 6.063 | 61 |
| 15.10 | 5.864 | 62 |
| 15.42 | 5.741 | 51 |
| 15.84 | 5.592 | 29 |
| 16.19 | 5.471 | 91 |
| 16.86 | 5.254 | 88 |
| 17.42 | 5.087 | 25 |
| 17.69 | 5.011 | 31 |
| 18.35 | 4.831 | 100 |
| 19.66 | 4.511 | 43 |
| 20.11 | 4.411 | 37 |
| 20.93 | 4.240 | 38 |
| 21.32 | 4.165 | 33 |
| 22.71 | 3.913 | 36 |
| 23.31 | 3.813 | 40 |
| 23.81 | 3.734 | 31 |
| 24.23 | 3.671 | 28 |
| 24.60 | 3.616 | 38 |
| 25.13 | 3.541 | 87 |
| 25.74 | 3.458 | 39 |
| 27.19 | 3.277 | 38 |

Crystalline form IV of posaconazole obtained above has an attenuated total reflectance IR spectrum with absorption bands at 3647, 3472, 2867, 1687, 1512, 1230, 1136, 916, 853, 819 and 681 cm$^{-1}$ (±2 cm$^{-1}$; FIG. 2).

The obtained crystalline form IV was subjected to differential thermal analysis. As can be seen in FIG. 3 (lower curve), crystalline form IV shows a significant dehydration endotherm between 25° C. and 105° C. with a subsequent endothermic conversion at 116° C. ($T_{onset}$ 113.3° C.) followed by a peak at 119.6° C. ($T_{onset}$ 117.5° C.) and melting at 170.5° C. with a $T_{onset}$ of 167.9° C. (10° C./minute, open pan).

Figure 4:
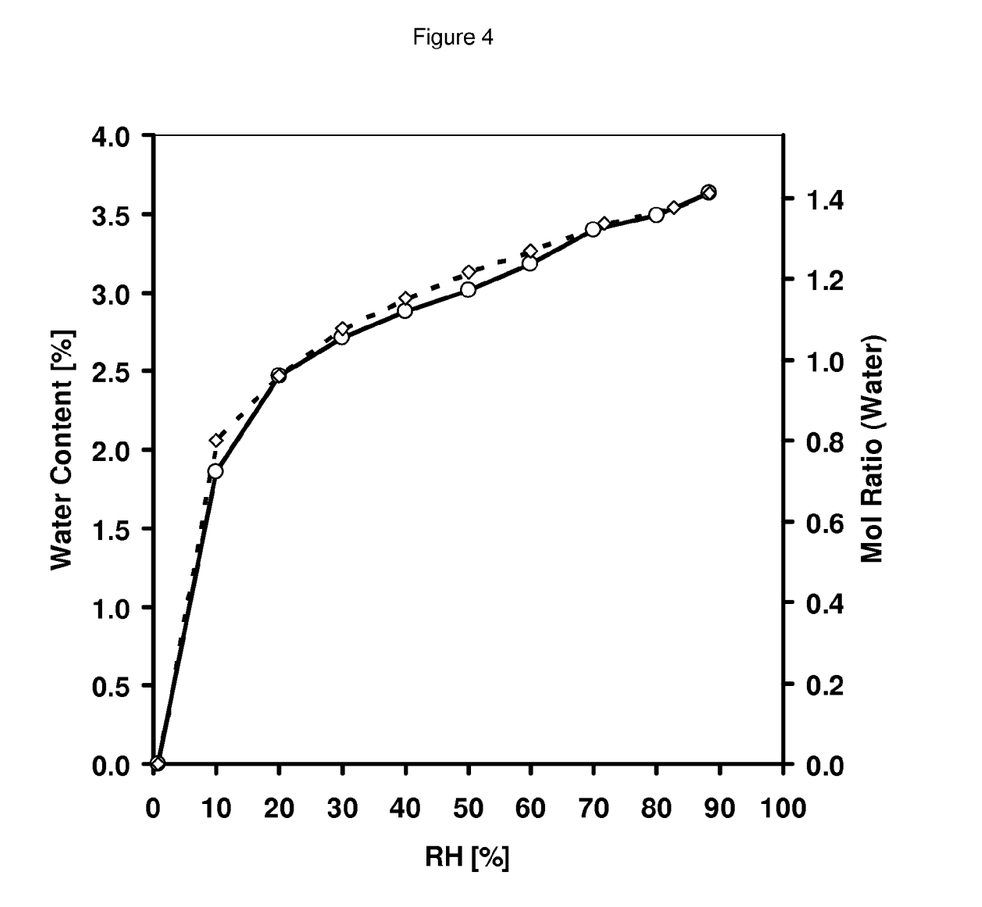
FIG. 4: Moisture sorption isotherm of form IV of posaconazole. The water content in % (left hand ordinate) and the mol ratio of water (right hand ordinate) are plotted versus the relative humidity in %. The dotted line refers to desorption, while the solid line refers to sorption.

The water content of the obtained crystalline form IV was 2.43%. The moisture sorption isotherm of crystalline form IV shows a distinct step over 0.6 mol water uptake/loss between 0 and 10% relative humidity. The maximum water content peaks at 3.7% at 90% relative humidity, which corresponds to a water mol ratio of 1.5 (FIG. 4).

Example 2

500 mg of posaconazole form III, prepared by the method of example 6 described in U.S. Pat. No. 6,958,337, were suspended in a solution consisting of 10 ml of water and 2.5 ml of methanol. The mixture was stirred at ambient temperature for 3 days. The white suspension was filtered and the product was dried in vacuum overnight. The product was analyzed by XRPD and found to be a mixture of form III and IV. The mixture of the two forms was again suspended in a solution consisting of 10 ml of water and 2.5 ml of methanol and stirred at ambient temperature overnight. Afterwards the solid was filtered off and dried in vacuum overnight to yield pure crystalline form IV of posaconazole.

Example 3

54 mg of posaconazole form III, prepared by the method of example 6 described in U.S. Pat. No. 6,958,337, were suspended in 2 ml water and seeded with form IV. The mixture was stirred at 25° C. for 48 hours. The white suspension was filtered and dried in air to yield 38 mg of form IV.

Example 4

250 mg of posaconazole form III, prepared by the method of example 6 described in U.S. Pat. No. 6,958,337, were suspended in a solution consisting of 5 ml of water and 1.25 ml of methanol. After seeding with a form IV crystal, obtained by the method of example 2 above, the obtained mixture was stirred at about 50° C. for 3 hours. The mixture was then cooled down to ambient temperature and the solid was collected by filtration and dried in vacuum at ambient temperature overnight yielding 245 mg of substantially pure form IV of posaconazole. The product was again suspended in a solution consisting of 5 ml of water and 1.25 ml of methanol and then stirred at ambient temperature overnight. The white solid was filtered off and dried in vacuum overnight to yield 240 mg of crystalline form IV.

Example 5

The solubility of crystalline form IV was determined by the equilibrium solubility method. A saturated solution of form IV, obtained by stirring 250 mg form IV in 6 ml water overnight, was prepared. The sample was filtered through a 0.45 μm membrane filter and the concentration of form IV in the filtrate was measured using a Perkin Elmer Lambda 35 UV/VIS spectrophotometer (λ=260 nm). The solubility of form IV was found to be 2.1 μg/ml which is more than two times higher than that of form I.

Example 6

The stability of form IV in an aqueous pharmaceutical composition was investigated. 240 mg form IV were suspended in a 4 ml aqueous suspension consisting of a mixture of 19 mg sodium benzoate, 3 mg citric acid, 19 mg xanthan gum, 60 mg Polysorbat 80, 600 mg glycerine and 2 g liquid glucose. The suspension was stirred at ambient temperature for 1 week. Crystalline form IV remained stable in the suspension and no other form could be detected by XRPD.

Example 7

Determination of the Specific Surface Area of Crystalline Form IV

Specific surface area measurement was performed with the equipment NOVA 2000 as commercially available from Quantachrome Instruments using the BET method and Nitrogen as the absorbed gas at 77° K (i.e. −196.15° C.) as described e.g. by Medema J, Campagne A.: A Simple Method to Determine Cumulative Surface-Area Distributions of Porous Solids; Journal of Catalysis, Volume 8, Issue 2, pp. 120, 1967. Crystalline form IV of posaconazole was prepared according to Example 4. Crystalline form I was prepared by the method of example 3 described in U.S. Pat. No. 6,958,337. The results are shown in Table 2 below:

TABLE 2

| Specific Surface Area (in m²/g) | |
|---|---|
| Crystalline Form IV of posaconazole | Crystalline Form I of posaconazole |
| 15.5 | 1.5 |
| 15.7 | 1.6 |

Table 2 shows that crystalline form IV of posaconazole has an about 10-fold larger specific surface area when compared to crystalline form I of posaconazole. As explained above, this higher specific surface area value results in a higher dissolution rate which is expected to lead to an improved bioavailability of form IV when compared to that of known form I.

Example 8

Determination of Median Particle Size of Form IV

Crystalline form IV as obtained by Example 4 was used to prepare 25 ml of a suspension as follows:

| Ingredient | Quantity (in g) |
|---|---|
| Posaconazole Form IV | 1.000 |
| Polysorbate 80 | 0.250 |
| Simethicone | 0.075 |
| Xanthan Gum | 0.075 |
| Sodium Benzoate | 0.050 |
| Sodium Citrate Dihydrate | 0.015 |
| Citric Acid Monohydrate | 0.038 |
| Liquid Glucose | 8.750 |
| Glycerol | 2.500 |
| Titanium Dioxide | 0.100 |
| Purified Water | 12.148 |

The suspension was prepared as follows: 40% of the final amount of Polysorbat 80 and 40% of the final amount of simethicone were mixed and dissolved and/or dispersed in about 12% of the final amount of purified water and homogenized with Ultra Turrax (30 seconds; 27,000 rpm). Subsequently, 1 g of the form IV of posaconazole, i.e. in its non-micronized form, were suspended or dispersed in this mixture under homogenization by Ultra Turrax (27,000 rpm, 2 minutes). The remaining 60% of Polysorbat 80 and of simethicone and 32% of the final amount of the purified water were added and mixed followed by the addition of sodium benzoate, sodium citrate dihydrate and citric acid monohydrate. After further mixing, xanthan gum was added to the mixture under stirring, followed by a 30 minutes phase of hydratization without mixing. Subsequently, glycerol and liquid glucose as well as titanium dioxide and the remaining portion of 56% of the final amount of purified water were added under mixing with a suitable homogenizer until a uniform suspension was obtained.

25 ml of a similar suspension were prepared analogously using non-micronized crystalline form I of posaconazole which was prepared by the method of example 3 described in U.S. Pat. No. 6,958,337.

Additionally, NOXAFIL® oral suspension (40 mg/ml) as commercially available from Medizone Germany GMBH (US product) was used to determine the particle size distribution of micronized form I of posaconazole which was contained in this known suspension.

The particle size distribution (Malvern) was measured according to the USP 32 (2009) method <429> and EP 6 (2008) method 2.9.31. based on the diffraction of laser by particles using a Mastersizer 2000S liquid dispersion system. The particle size measurement was started after ultrasonic treatment of the sample for 5 min. The results are shown in Table 3 below:

TABLE 3

| Polymorphic form of posaconazole | Median particle size (d (0.5)-value in μm) |
| --- | --- |
| Crystalline Form IV (non-micronized) | 0.15 |
| Crystalline Form I (non-micronized) | 12.88 |
| Crystalline Form I (micronized as contained in NOXAFIL ®) | 2.06 |

Table 3 shows that non-micronized crystalline form IV has an about 90-fold smaller median particle size when compared to non-micronized form I. Also, polymorphic form IV of posaconazole has an about 10-fold smaller median particle size when compared to micronized form I. This smaller particle size of crystalline form IV contributes to an improved dissolution behaviour of form IV, i.e. to a faster dissolution of form IV when compared to form I as is described in Example 9 below and shown in FIG. 6.

Example 9

Dissolution of Crystalline Form IV as Compared to Crystalline Form I

The liquid suspensions containing non-micronized crystalline form IV or non-micronized crystalline form I as well as the NOXAFIL® oral suspension containing micronized crystalline form I described in Example 8 were tested for their dissolution behaviour.

Dissolution was tested according to USP 32 (2009) method <711> (USP apparatus II (Paddle); 25 rpm; dissolution medium: 0.3% SLS aqueous solution). Posaconazole concentrations were determined with an online photometer (UV absorption at 260 nm).

The results are shown in Table 4 below wherein values are the amount of posaconazole dissolved in %, and in more detail in FIG. 6 wherein the amount of posaconazole dissolved in % is plotted versus time in minutes.

TABLE 4

| Time (min) | Crystalline Form IV non-micronized | Crystalline Form I non-micronized | Crystalline Form I micronized |
| --- | --- | --- | --- |
| 3 | 82% | 29% | 54% |
| 25 | 100% | 61% | 92% |

As shown in Table 4 and in FIG. 6, non-micronized crystalline form IV of posaconazole shows a distinctly faster dissolution when compared to non-micronized crystalline form I. Crystalline form IV additionally shows a similar, i.e. slightly faster rate of dissolution when compared to micronized form I as contained in the commercialized NOXAFIL® oral suspension.

As an improved dissolution behaviour is considered to enhance bioavailability, non-micronized crystalline form IV is expected to have an improved bioavailability as compared to that of non-micronized form I—and a similar and probably slightly better bioavailability as compared to that of micronized form I as contained in known posaconazole suspensions.

The invention claimed is:

1. A crystalline form IV of posaconazole having at least one of an X-ray powder diffraction pattern comprising peaks at 2-theta angles of 3.2°±0.2°, 6.6°±0.2°, 10.9°±0.2°, 16.9°±0.2°, 18.4°±0.2° and 25.1°±0.2° or an attenuated total reflectance infrared spectrum comprising absorption bands at wavenumbers of 3647 cm$^{-1}$±2 cm$^{-1}$, 3472 cm$^{-1}$±2 cm$^{-1}$, 2867 cm$^{-1}$±2 cm$^{-1}$, 1687 cm$^{-1}$±2 cm$^{-1}$, 1512 cm$^{-1}$±2 cm$^{-1}$, 1230 cm$^{-1}$±2 cm$^{-1}$, 1136 cm$^{-1}$±2 cm$^{-1}$, 916 cm$^{-1}$±2 cm$^{-1}$, 853 cm$^{-1}$±2 cm$^{-1}$, 819 cm$^{-1}$±2 cm$^{-1}$ and 681 cm$^{-1}$±2 cm$^{-1}$.

2. The crystalline form IV of posaconazole according to claim 1, having a specific surface area of about 10 to 25 m$^2$/g±0.5 m$^2$/g.

3. The crystalline form IV of posaconazole according to claim 1, having a median particle size of about 0.1 to 0.2 μm±0.05 μm.

4. A process for the preparation of crystalline form IV of posaconazole comprising the steps of:
   (a) providing a suspension or dispersion of:
      (i) crystalline form III of posaconazole or amorphous posaconazole or a mixture thereof; and
      (ii) water or a mixture of water and methanol; and
   (b) allowing the posaconazole provided in step (i) to transform to crystalline form IV at a temperature of at most 60° C., wherein the crystalline form IV of posaconazole has at least one of an X-ray powder diffraction pattern comprising peaks at 2-theta angles of 3.2°±0.2°, 6.6°±0.2°, 10.9°±0.2°, 16.9°±0.2°, 18.4°±0.2° and 25.1°±0.2° or an attenuated total reflectance infrared spectrum comprising absorption bands at wavenumbers of 3647 cm$^{-1}$±2 cm$^{-1}$, 3472 cm$^{-1}$±2 cm$^{-1}$, 2867 cm$^{-1}$±2 cm$^{-1}$, 1687 cm$^{-1}$±2 cm$^{-1}$, 1512 cm$^{-1}$±2 cm$^{-1}$, 1230 cm$^{-1}$±2 cm$^{-1}$, 1136 cm$^{-1}$±2 cm$^{-1}$, 916 cm$^{-1}$±2 cm$^{-1}$, 853 cm$^{-1}$±2 cm$^{-1}$, 819 cm$^{-1}$±2 cm$^{-1}$ and 681 cm$^{-1}$±2 cm$^{-1}$.

5. A process for the preparation of crystalline form IV of posaconazole comprising the steps of:
   (a) providing a suspension or dispersion of:
      (i) crystalline form I or form II of posaconazole or a mixture thereof;
      (ii) water or a mixture of water and methanol; and
      (iii) seed crystals of crystalline form IV of posaconazole; and
   (b) allowing the posaconazole provided in step (i) to transform to crystalline form IV at a temperature of at most 60° C., wherein the crystalline form IV of posaconazole has at least one of an X-ray powder diffraction pattern comprising peaks at 2-theta angles of 3.2°±0.2°, 6.6°±0.2°, 10.9°±0.2°, 16.9°±0.2°, 18.4°±0.2° and 25.1°±0.2° or an attenuated total reflectance infrared spectrum comprising absorption bands at wavenumbers of 3647 cm$^{-1}$±2 cm$^{-1}$, 3472 cm$^{-1}$±2 cm$^{-1}$, 2867 cm$^{-1}$±2 cm$^{-1}$, 1687 cm$^{-1}$±2 cm$^{-1}$, 1512 cm$^{-1}$±2 cm$^{-1}$, 1230 cm$^{-1}$±2 cm$^{-1}$, 1136 cm$^{-1}$±2 cm$^{-1}$, 916 cm$^{-1}$±2 cm$^{-1}$, 853 cm$^{-1}$±2 cm$^{-1}$, 819 cm$^{-1}$±2 cm$^{-1}$ and 681 cm$^{-1}$±2 cm$^{-1}$.

6. The process according to claim 4, wherein the step (b) is conducted at a temperature of 10° C. to 60° C.

7. The process according to claim 5, wherein the step (b) is conducted at a temperature of 10° C. to 60° C.

8. The process according to claim 4, wherein the step (b) is conducted at a temperature of 15° C. to 50° C.

9. The process according to claim 5, wherein the step (b) is conducted at a temperature of 15° C. to 50° C.

10. A pharmaceutical composition comprising crystalline form IV of posaconazole and optionally a pharmaceutically acceptable carrier, wherein the crystalline form IV of posaconazole has at least one of an X-ray powder diffraction pattern comprising peaks at 2-theta angles of 3.2°±0.2°, 6.6°±0.2°, 10.9°±0.2°, 16.9°±0.2°, 18.4°±0.2° and 25.1°±0.2° or an attenuated total reflectance infrared spectrum comprising absorption bands at wavenumbers of 3647 cm$^{-1}$±2 cm$^{-1}$, 3472 cm$^{-1}$±2 cm$^{-1}$, 2867 cm$^{-1}$±2 cm$^{-1}$, 1687 cm$^{-1}$±2 cm$^{-1}$, 1512 cm$^{-1}$±2 cm$^{-1}$, 1230 cm$^{-1}$±2 cm$^{-1}$, 1136

$cm^{-1}\pm 2\ cm^{-1}$, 916 $cm^{-1}\pm 2\ cm^{-1}$, 853 $cm^{-1}\pm 2\ cm^{-1}$, 819 $cm^{-1}\pm 2\ cm^{-1}$ and 681 $cm^{-1}\pm 2\ cm^{-1}$.

11. The pharmaceutical composition according to claim 10, wherein the pharmaceutical composition is in the form of an aqueous suspension or dispersion.

12. The pharmaceutical composition according to claim 11, further comprising a non-ionic surfactant and optionally at least one thickening agent.

13. The pharmaceutical composition according to claim 10, formulated for treating or preventing a fungal infection.

14. A medicament comprising crystalline form IV of posaconazole, wherein the crystalline form IV of posaconazole has at least one of an X-ray powder diffraction pattern comprising peaks at 2-theta angles of 3.2°±0.2°, 6.6°±0.2°, 10.9°±0.2°, 16.9°±0.2°, 18.4°±0.2° and 25.1°±0.2° or an attenuated total reflectance infrared spectrum comprising absorption bands at wavenumbers of 3647 $cm^{-1}\pm 2\ cm^{-1}$, 3472 $cm^{-1}\pm 2\ cm^{-1}$, 2867 $cm^{-1}\pm 2\ cm^{-1}$, 1687 $cm^{-1}\pm 2\ cm^{-1}$, 1512 $cm^{-1}\pm 2\ cm^{-1}$, 1230 $cm^{-1}\pm 2\ cm^{-1}$, 1136 $cm^{-1}\pm 2\ cm^{-1}$, 916 $cm^{-1}+2\ cm^{-1}$, 853 $cm^{-1}\pm 2\ cm^{-1}$, 819 $cm^{-1}\pm 2\ cm^{-1}$ and 681 $cm^{-1}\pm 2\ cm^{-1}$.

15. The medicament according to claim 14, formulated for treating or preventing a fungal infection.

16. A method of treating or preventing a fungal infection by administering a therapeutically effective amount of crystalline form IV of posaconazole to a patient in need thereof, wherein the crystalline form IV of posaconazole has at least one of an X-ray powder diffraction pattern comprising peaks at 2-theta angles of 3.2°±0.2°, 6.6°±0.2°, 10.9°±0.2°, 16.9°±0.2°, 18.4°±0.2° and 25.1°±0.2° or an attenuated total reflectance infrared spectrum comprising absorption bands at wavenumbers of 3647 $cm^{-1}\pm 2\ cm^{-1}$, 3472 $cm^{-1}\pm 2\ cm^{-1}$, 2867 $cm^{-1}\pm 2\ cm^{-1}$, 1687 $cm^{-1}\pm 2\ cm^{-1}$, 1512 $cm^{-1}\pm 2\ cm^{-1}$, 1230 $cm^{-1}\pm 2\ cm^{-1}$, 1136 $cm^{-1}+2\ cm^{-1}$, 916 $cm^{-1}\pm 2\ cm^{-1}$, 853 $cm^{-1}\pm 2\ cm^{-1}$, 819 $cm^{-1}\pm 2\ cm^{-1}$ and 681 $cm^{-1}\pm 2\ cm^{-1}$.

* * * * *